(12) United States Patent
Joseph et al.

(10) Patent No.: US 7,939,130 B2
(45) Date of Patent: May 10, 2011

(54) METHOD OF FORMING A FILM OF NANOPARTICLES INTERLINKED WITH EACH OTHER USING A POLYFUNCTIONAL LINKER

(75) Inventors: Yvonne Joseph, Stuttgart (DE);
Heinz-Georg Nothofer, Stuttgart (DE);
Tobias Vossmeyer, Esslingen (DE);
Jurina Wessels, Stuttgart (DE); Akio Yasuda, Esslingen (DE)

(73) Assignee: Sony Deutschland GmbH, Berlin (DE)

( * ) Notice: Subject to any disclaimer, the term of this patent is extended or adjusted under 35 U.S.C. 154(b) by 1175 days.

(21) Appl. No.: 11/552,326

(22) Filed: Oct. 24, 2006

(65) Prior Publication Data
US 2007/0231947 A1    Oct. 4, 2007

(30) Foreign Application Priority Data

Mar. 31, 2006   (EP) .................................. 06006881

(51) Int. Cl.
*B05D 7/00* (2006.01)
(52) U.S. Cl. ........................................ 427/217; 977/811
(58) Field of Classification Search ............. 427/213.33, 427/213.34, 212, 214, 216
See application file for complete search history.

(56) References Cited

U.S. PATENT DOCUMENTS

| | | | |
|---|---|---|---|
| 3,875,170 A * | 4/1975 | Matsumoto et al. | .......... 546/187 |
| 5,589,537 A | 12/1996 | Golden et al. | |
| 6,458,327 B1 * | 10/2002 | Vossmeyer | .................. 422/68.1 |
| 2002/0127756 A1* | 9/2002 | Wessels et al. | ................. 438/39 |
| 2002/0132361 A1* | 9/2002 | Vossmeyer et al. | ........... 436/151 |
| 2003/0096113 A1 | 5/2003 | Jacobson et al. | |
| 2004/0010864 A1 | 1/2004 | Vic et al. | |

FOREIGN PATENT DOCUMENTS

| | | |
|---|---|---|
| EP | 1 022 560 A1 | 7/2000 |
| EP | 1 215 205 A1 | 6/2002 |
| EP | 1 278 061 A1 | 1/2003 |
| WO | WO 96/07487 | 3/1996 |

OTHER PUBLICATIONS

Almirall et al., Molecular recognition of a self-assembled monolayer of a polydithiocarbamate derivative of beta-cyclodextrin on silver, Electrochemistry Communications, 1990, p. 10-13.*

Zhao et al., Dithiocarbamate assembly on gold, JACS, 2005, 7328-7329.*

Brust et al., Self-Assembled Gold Nanoparticle Thin Films with Nonmetallic Optical and Electronic Properties, Langmuir, 1998, p. 5425-5429.*

* cited by examiner

*Primary Examiner* — Frederick J Parker
*Assistant Examiner* — Tabatha Penny
(74) *Attorney, Agent, or Firm* — Oblon, Spivak, McClelland, Maier & Neustadt, L.L.P.

(57) ABSTRACT

The present invention relates to a method of forming a film of nanoparticles interlinked with each other using a polyfunctional linker.

31 Claims, 4 Drawing Sheets

Figure 1:
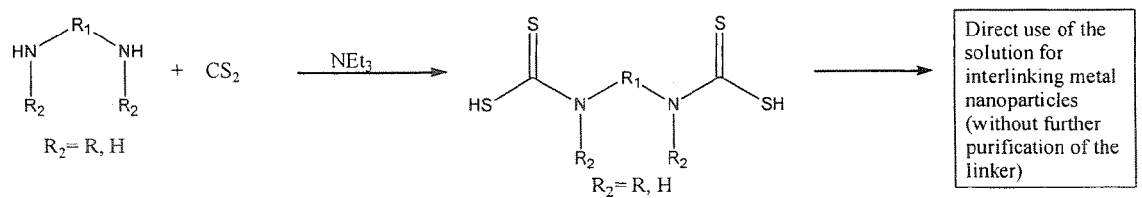

METHOD OF FORMING A FILM OF NANOPARTICLES INTERLINKED WITH EACH OTHER USING A POLYFUNCTIONAL LINKER

The present invention relates to a method of forming a film of nanoparticles interlinked with each other using a polyfunctional linker.

Nanoparticle films are useful in many applications, such as molecular electronic devices, for example chemical sensors. In order to be stable, nanoparticles in such films can be capped or interlinked by capping molecules or linker molecules. One method of forming such nanoparticle films which are interlinked with molecules is the layer-by-layer self-assembly (EP 1 022 560). Here, substrates are alternately immersed into nanoparticle solutions/dispersions and solutions of organic molecules, such as dithiols (Joseph, et al., J. Phys. Chem. B 2003, 107,7406) and bis(dithiocarbamates) (Wessels et al., J. An. Chem. Soc., 2004, 126, 3349). This results in an assembly of the material in a nanoparticle film wherein the nanoparticles are interlinked. Whilst the nanoparticles in the film are most important for the conductivity and the high surface to volume ratio of the materials, the organic molecules functioning as linkers or capping molecules determine the physical and chemical properties of the materials (EP 1 215 485). Therefore, a broad variety of materials with tuned properties can be achieved by choosing appropriate linker molecules. Commonly, these organic linker molecules have to be synthesized and purified before hand. Zhao et al. (J. Am. Chem. Soc. 2005; 127; 7328) describe the self-assembly of a dithiocarbamate monolayer on gold surfaces. In this publication, the samples were prepared from a solution containing commercially available secondary amines and carbon disulfide which undergo a reaction to form in-situ dithiocarbomate molecules. This publication is not concerned with the formation of nanoparticulate films.

The layer-by-layer self-assembly process referred to above has many advantages. The main advantage is the reproducibility of the preparation and the structural control of the film. However, the major disadvantage of such an assembly method is that the organic linker molecules have to be synthesized, purified and isolated beforehand, whereupon they are used as a solution into which a substrate is dipped in alternation with a dispersion of nanoparticles. The synthesis, purification and isolation is time consuming and labor intensive and therefore un-economical.

It was therefore an object of the present invention to provide for a fast and cheap way to form nanoparticle films. It was also an object of the present invention to provide for a method of forming nanoparticle films which require fewer steps than the methods known from the prior art.

All these objects are solved by a method of forming a film of nanoparticles interlinked with each other using a polyfunctional linker, characterized in that said polyfunctional linker is generated in a reaction mixture which reaction mixture is used for interlinking said nanoparticles, without purification of said polyfunctional linker.

In one embodiment the method according to the present invention, comprising the following steps:
  a) providing a precursor capable of producing said polyfunctional linker,
  b) in a reaction mixture containing said precursor, preferably in a solution of said precursor, inducing said precursor to produce said polyfunctional linker,
  c) using said reaction mixture of step b) without purification to interlink nanoparticles.

Preferably, step c) is performed immediately after step b) has finished.

In another embodiment step c) is performed together with step b) by including nanoparticles in said reaction mixture of step b) from the start of step b), or by adding nanoparticles to said reaction mixture of step b) in the course of step b).

In one embodiment a film of nanoparticles interlinked by said polyfunctional linker is formed on a substrate by immersing said substrate in said reaction mixture.

In one embodiment a film of nanoparticles interlinked by said polyfunctional linker is formed on a substrate by alternately immersing said substrate in said reaction mixture and a dispersion of nanoparticles.

In another embodiment a film of nanoparticles interlinked by said polyfunctional linker is formed on a substrate by immersing said substrate in said reaction mixture which also has nanoparticles in it.

In one embodiment said polyfunctional linker has at least two functional groups each of which enables said linker to bind to a nanoparticle, such that upon binding of said functional groups to nanoparticles, at least two nanoparticles are linked thereby.

In one embodiment said polyfunctional linker is a bifunctional linker in having two functional groups each of which enables said linker to bind to a nanoparticle, and further characterized in that said bifunctional linker has the general form:

Z—R—Z, wherein R denotes an organic rest and Z denotes a functional group having a binding affinity to metal atoms on the nanoparticle surface, wherein, more preferably, said bifunctional linker Z—R—Z is produced from a reaction of its precursor

X—R—X with B,
wherein X denotes a functional group having no binding affinity to metal atoms on the nanoparticle surface, R denotes an organic rest and B denotes a reactant which, upon reaction with said precursor, produces said bifunctional linker.

In one embodiment said precursor X—R—X is reacted in a reaction mixture with B under reaction conditions allowing the formation of the bifunctional linker molecule, whereupon a substrate is alternately immersed in said reaction mixture and a dispersion of nanoparticles allowing the formation of nanoparticles interlinked by said bifunctional linker, to form a film of nanoparticles interlinked by said bifunctional linker on said substrate.

In another embodiment said precursor X—R—X is reacted in a reaction mixture with B and nanoparticles under reaction conditions allowing the formation of said bifunctional linker and the formation of nanoparticles interlinked by said bifunctional linker, into which reaction mixture a substrate is immersed to form a film of nanoparticles interlinked by said bifunctional linker on said substrate.

Preferably, said bifunctional linker is selected from the group comprising bis(dithiocarbamates), bis(xanthates), bis(dithiocarboxylic acids), bis(trithiocarbonates), bis(dithiooxamides), and bis(thiuronium salts), wherein for said bis(dithiocarbamates) Z is —NR—CSSH, X is —NH—R, and B is $CS_2$,
wherein for said bis(xanthates) Z is —O—CSSH, X is —OH and B is $CS_2$,
wherein for said bis(dithiocarboxylic acids) Z is —CSSH, X is MgBr, and B is $CS_2$,
wherein for said bis(trithiocarbonates) Z is —S—CSSH, X is SH, and B is $CS_2$, wherein for said bis(dithiooxamides) Z is —NH—C(S)—C(S)—NH—R, X is $NH_2$, and B is $NH_2$—C(S)—C(S)—$NH_2$, and wherein for said bis(thiuronium salts) Z is —$S^+$(—NH2)(=NH)$X^-$, X is Br, Cl or I, and B is $NH_2$—C(S)—$NH_2$, and wherein for any of the aforementioned compounds R is an organic rest.

In one embodiment said reaction conditions allowing the formation of said bifunctional linker molecule for said bis(dithiocarbamates) are triethylamine as a solvent and room temperature, for said bis(xanthates) are NaH at 40-80° C., preferably 50-70° C. and more preferably approximately 60° C.

for said bis(dithiocarboxylic acids) are room temperature, for said bis(trithiocarbonates) are NaH at 40-80° C., preferably 50-70° C., more preferably approximately 60° C., for said bis(dithiooxamides) are room temperature, and for said bis(thiuronium salts) are 60° C.-100° C., preferably 70-90° C., and more preferably approximately 80° C., and wherein for any of the aforementioned compounds, said reaction conditions allowing the formation of nanoparticles interlinked by said bifunctional linker is room temperature.

In one embodiment said polyfunctional linker has at least three functional groups each of which enables said linker to bind to a nanoparticle, such that, upon binding of said functional groups to nanoparticles, at least three nanoparticles are linked thereby.

In one embodiment said polyfunctional linker is a trifunctional linker in having three functional groups each of which enables said linker to bind to a nanoparticle, and further characterized in that said trifunctional linker has the general form

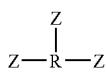

wherein R denotes an organic rest and Z denotes a functional group having a binding affinity to metal atoms on the nanoparticle surface, wherein, preferably, said trifunctional linker

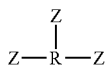

is produced from a reaction of its precursor

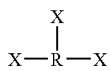

with B, wherein X denotes a functional group having no binding affinity to metal atoms on the nanoparticle surface, R denotes an organic rest, and B denotes a reactant which, upon reaction with said precursor, produces said trifunctional linker, wherein, more preferably, said precursor

is reacted in a reaction mixture with B under reaction conditions allowing the formation of the trifunctional linker molecule, whereupon a substrate is alternately immersed in said reaction mixture and a dispersion of nanoparticles allowing the formation of nanoparticles interlinked by said trifunctional linker to form a film of nanoparticles interlinked by said trifunctional linker on said substrate.

In another embodiment said precursor

is reacted in a reaction mixture with B and nanoparticles under reaction conditions allowing the formation of said trifunctional linker and the formation of nanoparticles interlinked by said trifunctional linker, into which reaction mixture a substrate is immersed to form a film of nanoparticles interlinked by said trifunctional linker on said substrate.

Preferably, said trifunctional linker is selected from the group comprising tris(dithiocarbamates), tris(xanthates), tris(dithiocarboxylic acids), tris(trithiocarbonates), tris(dithiooxamides) and tris(thiuronium salts), wherein for said bis(dithiocarbamates) Z is —NR—CSSH, X is —NH—R, and B is $CS_2$, wherein for said bis(xanthates) Z is —O—CSSH, X is —OH and B is $CS_2$, wherein for said bis(dithiocarboxylic acids) Z is —CSSH, X is MgBr, and B is $CS_2$, wherein for said bis(trithiocarbonates) Z is —S—CSSH, X is SH, and B is $CS_2$, wherein for said bis(dithiooxamides) Z is —NH—C(S)—C(S)—NH—R, X is $NH_2$, and B is $NH_2$—C(S)—C(S)—$NH_2$, and wherein for said bis(thiuronium salts) Z is —$S^+$(—NH2)(=NH)$X^-$, X is Br, Cl or I, and B is $NH_2$—C(S)—$NH_2$, and wherein for any of the aforementioned compounds R is an organic rest.

In one embodiment said reaction conditions allowing the formation of said trifunctional linker molecule for said tris(dithiocarbamates) are triethylamine as a solvent and room temperature, for said tris(xanthates) are NaH at 40-80° C., preferably 50-70° C., and more preferably approximately 60° C., for said tris(dithiocarboxylic reagents) are room temperature, for said tris(trithiocarbonates) are NaH at 40-80° C., preferably 50-70° C., and more preferably approximately 60° C., for said tris(dithiooxamides) are room temperature, and for said tris(thiuronium salts) are 60° C.-100° C., preferably 70-90° C., and more preferably approximately 80° C., and wherein for any of the aforementioned compounds, said reaction conditions allowing the formation of nanoparticles interlinked by said trifunctional linker is room temperature.

In one embodiment said nanoparticles are nanoparticles having metal atoms on their surface.

Preferably, said nanoparticles are selected from the group comprising metal nanoparticles, metal oxide nanoparticles and semiconductor nanoparticles.

In one embodiment said nanoparticles are particles having average dimensions <1 Em, preferably ≦500 nm, preferably ≦300 nm, most preferably ≦100 nm.

As used herein, the term "purification" is meant to also include processes in which only an attempt is made to purify which, however, does not necessarily result in a fully purified product. The term "purification" is also meant to be used synonymously with the processes of "concentrating" or "isolating".

The term "polyfunctional linker", as used herein is meant to refer to a linker molecule in which there are at least two independent sites that enable the binding of said linker to nanoparticles, preferably metal-atoms or metal ions on such nanoparticles. "Functionality", in this sense, therefore refers to the capability of binding to nanoparticles.

The term "organic rest", as used herein is meant to refer to organic molecular rests selected from the group comprising straight- and branched-chain hydrocarbon groups having from 1 to 22 carbon atoms comprising either saturated or unsaturated hydrocarbon sub-units, such as methyl, ethyl, n-propyl, isopropyl, 2-propen-1-yl, 2-propyn-1-yl, dodecyl, hexadecyl or octadecyl, including substituted straight-chain hydrocarbon groups, such as 2-bromoethyl, 1-carboxyethyl, 2-carboxyethyl, 2-cyanoethyl, 2-hydroxy, 2-methoxyethyl, 2-nitroethyl, 2-mercaptoethyl, 2-phosphonoethyl, 2-sulfoethyl, 2,2, 2-trifluoroethyl or 2-vinyloxyethyl, cyclic hydrocarbon groups having from 3 to 12 carbon atoms comprising saturated hydrocarbon sub-units, such as cyclopropyl, cyclohexyl or adamantanyl, including substituted cyclic hydrocarbon groups, such as 1-carboxycyclopropyl, 4-hydroxycyclohexyl or glucityl, straight-chain and cyclic hydrocarbon groups having a total of 2 to 26 carbon atoms comprising saturated hydrocarbon sub-units and from 1 to 12 oxygen and/or nitrogen heteroatoms, such as 2-ethoxyethanol, 2-morpholinoethyl, 11-azido-3,6,9-trioxaundecyl or dodecaethyleneglycol, alkylaryl groups having a carbocyclic aromatic group of from 6 to 14 carbon atoms directly attached to an alkyl group of from 1 to 8 carbon atoms, such as benzyl, 2-phenylethyl, 3-phenylpropyl or 1-naphthylmethyl, including substituted carbocyclic aromatic groups directly attached to an alkyl group, such as (4-aminophenyl)-2-ethyl, (4-carboxyphenyl)-2-ethyl or (4-ethylphenyl)-2-ethyl, and alkylaryl groups having a heterocyclic aromatic group of from 3 to 13 carbon atoms and from 1 to 4 oxygen, nitrogen and/or sulfur atoms directly attached to an alkyl group of from 1 to 8 carbon atoms, such as (2-thiophenyl)methyl, indole-2-ethyl or (4-pyridyl)-2-ethyl.

The kind of "organic rest" chosen for the film formation determine the detailed physical and chemical properties of the respective nanoparticular film. Organic rests especially suited for chemiresistors used for chemical sensor applications are specified in EP 1 215 485, the entire contents of which is incorporated herein in its entirety by reference thereto.

The term "nanoparticle", as used herein, is meant to refer to particles the average dimensions of which are <1 μm, preferably ≦500 nm, more preferably ≦300 nm, and most preferably ≦100 nm.

The term "alternately immersing the substrate in a reaction mixture (of said polyfunctional linker) and a dispersion of nanoparticles", as used herein, is meant to refer to the process wherein said substrate is immersed into each of said reaction mixture and said dispersion of nanoparticles at least once, preferably twice, three times, four times, five times etc. A single cycle of "alternately immersing", as used above, therefore includes one immersion into said reaction mixture and one immersion into said dispersion of nanoparticles. If several such cycles are performed, there may, optionally, be a step of drying in between the various cycles. Such a process of "alternately immersing said substrate in said reaction mixture and a dispersion of nanoparticles", as used herein, is used synonymously with the term "layer-by-layer self-assembly".

The term "inducing said precursor to produce said polyfunctional linker", as used herein is meant to denote any process whereby said precursor is caused to produce the polyfunctional linker. Such process may for example involve a change of reaction conditions, such as temperature, solvent, or it may be the addition of a further reagent with which the precursor subsequently reacts to produce the polyfunctional linker. In one embodiment, the precursor is present in a reaction mixture such as a solution of the precursor, and a further reagent, e.g. $CS_2$ is added as a result of which the polyfunctional linker is produced.

The present inventors have surprisingly found that they were able to prepare nanoparticle films interlinked with polyfunctional linker molecules by layer-by-layer self-assembly wherein, the linker solution which is used for assembly, initially comprises precursor molecules which form the polyfunctional linker spontaneously, e.g. upon addition of a suitable reagent, such as $CS_2$, and wherein such a linker solution wherein the polyfunctional linker has been produced is used directly (in-situ) without further purification or isolation or concentration for the film assembly process. In one embodiment such linker solution may be used in the aforementioned layer-by-layer self-assembly process. Alternatively, in another embodiment, to such linker solution there may be added nanoparticles, and a substrate is subsequently immersed into such linker solution which additionally contains nanoparticles. Upon immersion, a nanoparticulate film interlinked by the polyfunctional linker molecules is precipitated by reaction of the nanoparticles with the linker molecules on the substrate. Both embodiments of this process can be conveniently performed under ambient conditions and therefore do not require extensive or complicated laboratory handling. Moreover, a large variety of polyfunctional linker molecules can be used in such way. The in-situ-generation and subsequent direct use obviates the need of further purification or isolation and therefore enables a fast and cheap way to form nanoparticle films.

Figure 2:
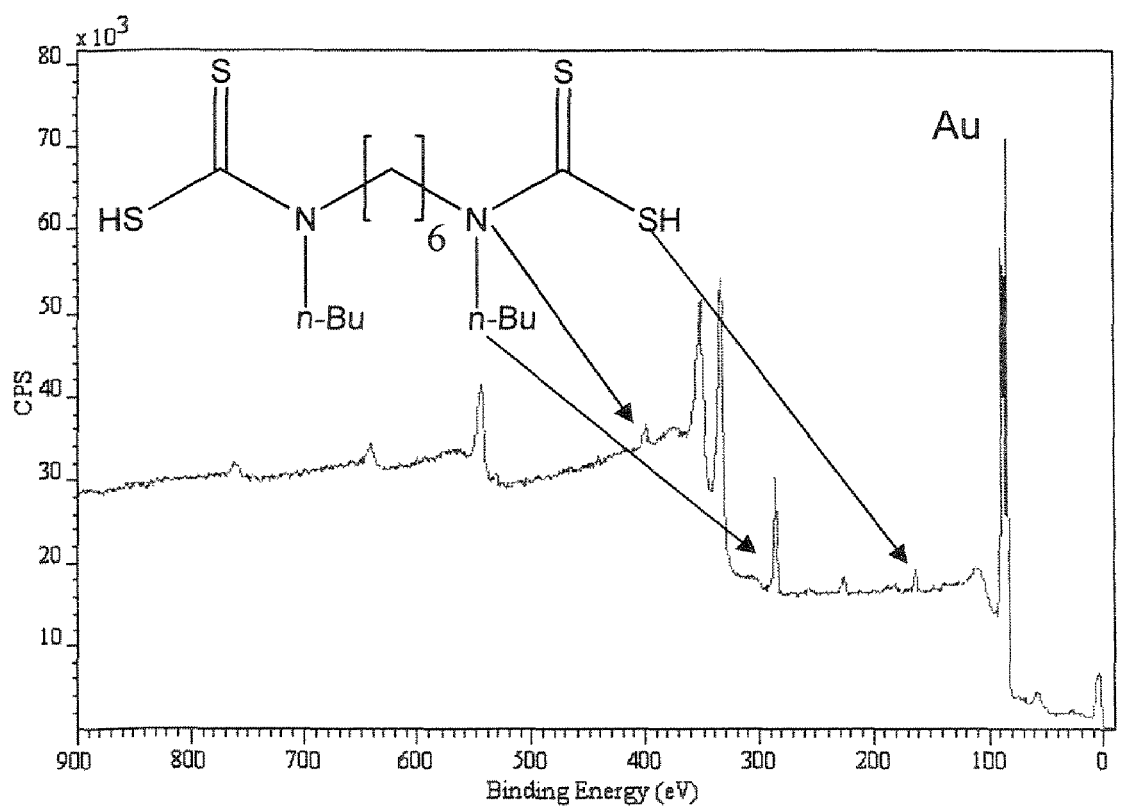
Figure 3:
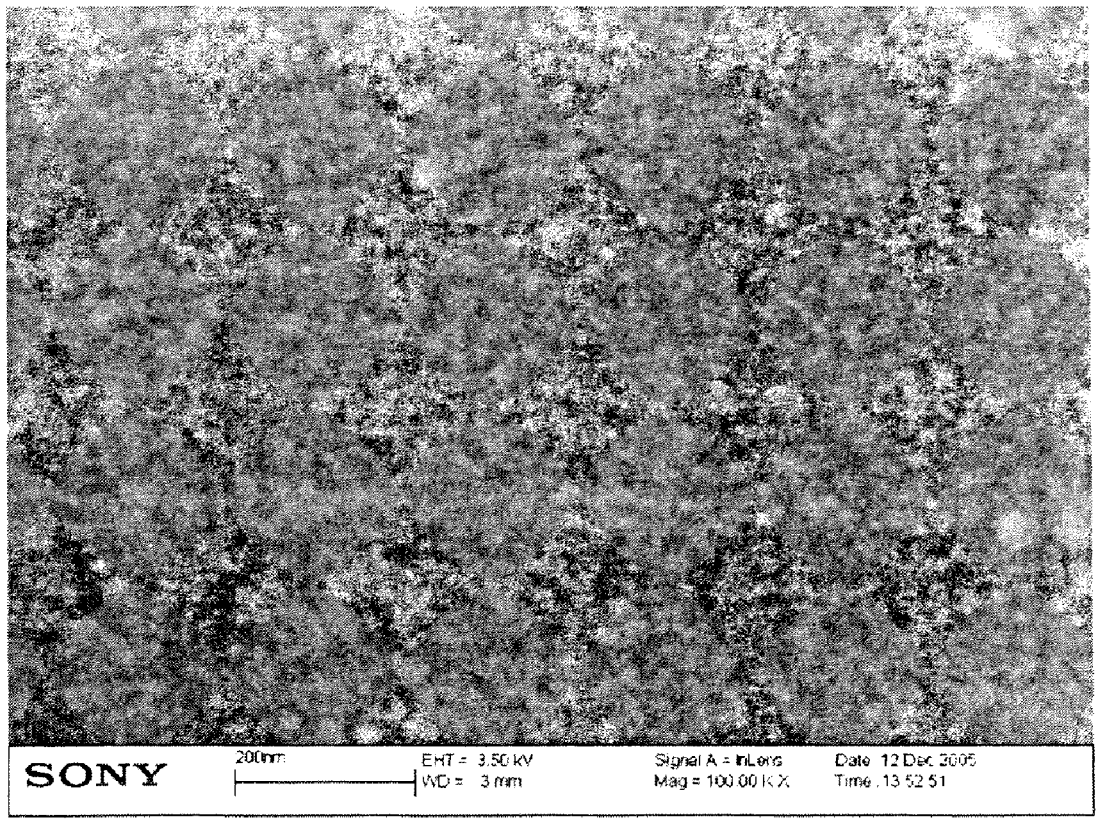
Figure 4:
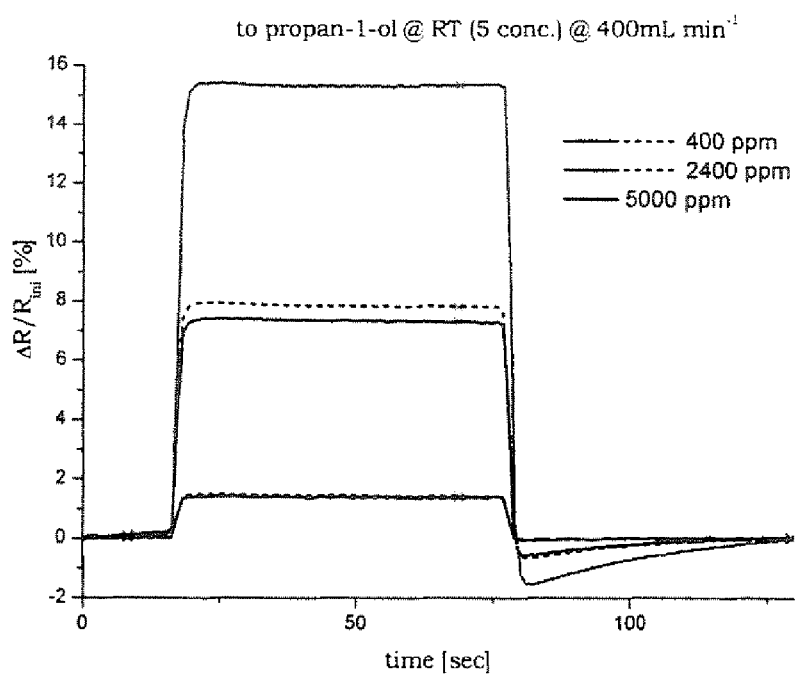
Figure 4:
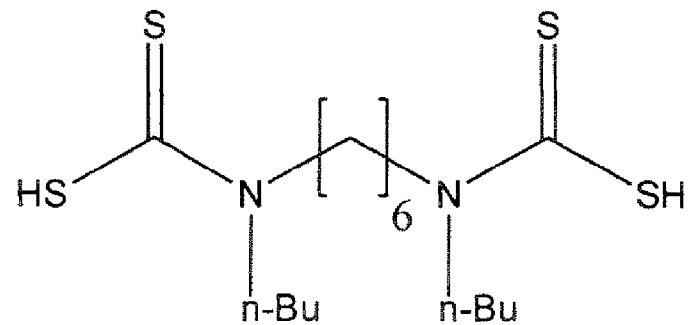

In the following, reference is made to the figures, wherein,

FIG. 1 shows the reaction in an exemplary linker solution forming in-situ bis(dithiocarbamates) from amines which were directly used for film assembly without further purification, FIG. 2 shows an X-Ray Photoelectron survey spectrum of a nanoparticulate film prepared with the in-situ formed indicated bis(dithiocarbamate), FIG. 3 shows an SEM image of the nanoparticle film assembled with the bis(dithiocarbamate) of FIG. 2, and FIG. 4 shows sensor responses of a bis(dithiocarbamate) sensor, wherein the structure of the linker which had been formed in-situ is also indicated (see also FIG. 2).

Moreover, reference is made to the following examples which are given to illustrate the invention not to limit the same.

EXAMPLES

1. An exemplary reaction was performed in accordance with FIG. 1, wherein bis(dithiocarbamates) from amines were formed in situ. This was performed by taking 1 ml of the solutions a, b and c mixing them together and adding 2 ml of toluene resulting in 5 ml of bis(dithiocarbamate) solution.

Solution a: 3.48 μl N,N'-Dibutyl-1,6-Hexanediamine in 5 ml toluene
Solution b: 4.36 μl CS₂ in 14 ml toluene
Solution c: 8.4 μl NEt3 in 12 ml toluene 2. The bis(dithiocarbamate) linker was used in a layer-by-layer self-assembly-process to interlink Au-nanoparticles. The film thus formed was examined using photoelectron spectroscopy which confirms the incorporation of the bis (dithiocarbamate) molecule and Au-nanoparticles in the film material. The XP spectrum of one sample is give in FIG. 2 as an example. Likewise, the film was examined using scanning electron microscopy, and the SEM image shown in FIG. 3 demonstrates that, indeed, a homogenous nanoparticle film was formed.

3. An exemplary scheme of a number of bifunctional or polyfunctional linkers can be summarized in the following scheme. Reaction a) is a layer-by-layer self-assembly process wherein, first, the polyfunctional linker is generated whereupon the reaction mixture is used directly without further purification for isolation or concentration in such layer-by-layer self-assembly process. The reaction b) denotes a reaction where a polyfunctional linker is generated, whilst nanoparticles are present in the reaction mixture. In this type of reaction, a substrate is then immersed in the reaction mixture, and the nanoparticulate film interlinked by the polyfunctional linker is precipitated on the substrate. Precipitation occurs spontaneously 1) Bifunctional Linker:

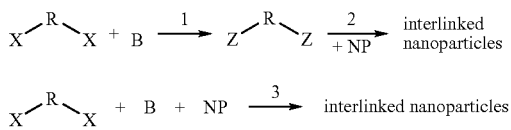

2) Polyfunctional Linker:

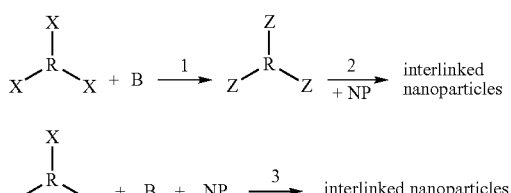

X = functional group, no or weak interaction with NP surface
B = reagent, no or weak interaction with NP surface
Z = functional group formed from A by reaction with B, strong interaction (=binding) with NP surface
R = organic rest,
1 = reaction conditions for forming the linker molecule in-situ
2 = reaction conditions for forming the nanoparticle network
3 = reaction conditions for forming the linker molecule in-situ and for forming the nanoparticle network NP = nanoparticles

EXAMPLES

Dithiocarbamates: X=—NH—R; B=CS₂; 1=NEt₃ @RT Z=—NR—CSSH
Xanthates: X=OH; B=CS₂; 1=NaH @60°, Z=—O—CSSH
Trithiocarbonates: X=SH; B=CS₂; 1=NaH @60°, Z=—S—CSSH
Dithiocarboxylic acids: X=MgBr; B=CS₂; 1=RT, Z=—CSSH
Dithiooxamides: X=NH₂; B=NH₂—C(S)—C(S)—NH₂; 1=RT, Z=—NH—C(S)—C(S)—NH—R
Thiuronium-Salts: X=Br, Cl, I; B=NH₂—C(S)—NH₂; 1=80°, Z=—S⁺(—NH2)(=NH)X⁻
2=e. g. layer by layer assembly @RT
3=e. g. precipitation @RT Moreover the resulting nanoparticle interlinked film material can be used as coating for a chemical sensor. Exemplary resulting sensor responses of the indicated bis(dithiocarbamate) chemiresistor are given in FIG. 4, showing the suitability of such nanoparticle interlinked films to be successfully used in chemical sensors.

Therefore in accordance with the method according to the present invention a variety of polyfunctional linker molecules can be formed in-situ which can then be used directly without further purification or concentration or isolation of the interlinking material. This approach enables a fast and cheap way to form nanoparticle films which makes such process amenable to mass production and processes on an industrial scale.

The features of the present invention disclosed in the specification, the claims and/or in the accompanying drawings, may, both separately, and in any combination thereof, be material for realising the invention in various forms thereof.

The invention claimed is:

1. A method of forming a film of nanoparticles interlinked with each other using a polyfunctional linker, characterized in that said polyfunctional linker is generated in a reaction mixture which reaction mixture is used for interlinking said nanoparticles, without purification of said polyfunctional linker, wherein said polyfunctional linker is a bifunctional linker selected from the group consisting of bis(dithiooxamides) and bis(thiuronium salts) or a trifunctional linker selected from the group consisting of tris(dithiooxamides) and tris(thiuronium salts).

2. The method according to claim 1, comprising the following steps:
a) providing a precursor capable of producing said polyfunctional linker,
b) in a reaction mixture containing said precursor, preferably in a solution of said precursor, inducing said precursor to produce said polyfunctional linker,
c) using said reaction mixture of step b) without purification to interlink nanoparticles.

3. The method according to claim 2, wherein step c) is performed immediately after step b) has finished.

4. The method according to claim 2, wherein step c) is performed together with step b) by including nanoparticles in said reaction mixture of step b) from the start of step b), or by adding nanoparticles to said reaction mixture of step b) in the course of step b).

5. The method according to claim 1, wherein a film of nanoparticles interlinked by said polyfunctional linker is formed on a substrate by immersing said substrate in said reaction mixture.

6. The method according to claim 3, wherein a film of nanoparticles interlinked by said polyfunctional linker is formed on a substrate by alternately immersing said substrate in said reaction mixture and a dispersion of nanoparticles.

7. The method according to claim 4, wherein a film of nanoparticles interlinked by said polyfunctional linker is formed on a substrate by immersing said substrate in said reaction mixture which also has nanoparticles in it.

8. The method according to claim 1, wherein said polyfunctional linker binds to a nanoparticle, such that at least two nanoparticles are linked thereby.

9. The method according to claim 1, wherein said nanoparticles have metal atoms on their surface.

10. The method according to claim 9, wherein said nanoparticles are selected from the group comprising metal nanoparticles, metal oxide nanoparticles and semiconductor nanoparticles.

11. The method according to claim 9, wherein said nanoparticles are particles having average dimensions <1 μm.

12. The method according to claim 1, wherein said polyfunctional linker is a bis(dithiooxamide).

13. The method according to claim 12, wherein the bis(dithiooxamide) is represented by the formula Z—R—Z, wherein Z is —NH—C(S)—C(S)—NH—R and R is an organic rest.

14. The method according to claim 1, wherein said polyfunctional linker is a bis(thiuronium salt).

15. The method according to claim 14, wherein the bis(thiuronium salt) is represented by the formula Z—R—Z, wherein Z is —S$^+$(—NH$_2$)(=NH)X$^-$, X is Br, Cl or I, and R is an organic rest.

16. The method according to claim 1, wherein said polyfunctional linker is a tris(dithiooxamide).

17. The method according to claim 16, wherein the trifunctional tris(dithiooxamide) is represented by the formula:

wherein Z is —NH—C(S)—C(S)—NH—R and R is an organic rest.

18. The method according to claim 1, wherein said polyfunctional linker is a tris(thiuronium salt).

19. The method according to claim 18, wherein the tris(thiuronium salt) is represented by the formula:

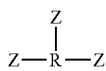

wherein Z is —S$^+$(—NH$_2$)(=NH)X$^-$, X is Br, Cl or I, and R is an organic rest.

20. The method according to claim 1, wherein said polyfunctional linked is said bifunctional linker and is produced from a reaction of a precursor represented by the formula:

with B, wherein X represents a functional group having no binding affinity to metal atoms on the nanoparticle surface, R represents an organic rest and B represents a reactant which, upon reaction with said precursor, produces said bifunctional linker.

21. The method according to claim 1, wherein said polyfunctional linker is said trifunctional linker and produced from a reaction of a precursor represented by the formula:

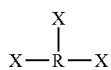

with B, wherein X denotes a functional group having no binding affinity to metal atoms on the nanoparticle surface, R denotes an organic rest, and B denotes a reactant which, upon reaction with said precursor, produces said trifunctional linker.

22. The method according to claim 20, wherein the polyfunctional linker is a bis(dithiooxamide), Z is —NH—C(S)—C(S)—NH—R, R is an organic rest, X is NH$_2$, and B is NH$_2$—C(S)—C(S)—NH$_2$.

23. The method according to claim 20, wherein the polyfunctional linker is a bis(dithiooxamide) and the reaction is conducted at room temperature.

24. The method according to claim 20, wherein the polyfunctional linker is a bis(thiuronium salt), Z is —S$^+$(—NH$_2$)(=NH)X$^-$, X is Br, Cl or I, R is an organic rest, and B is NH$_2$—C(S)—NH$_2$.

25. The method according to claim 20, wherein the polyfunctional linker is a bis(thiuronium salt) and the reaction is conducted at 60-100° C.

26. The method according to claim 21, wherein the polyfunctional linker is a tris(dithiooxamide), Z is —NH—C(S)—C(S)—NH—R, R is an organic rest, X is NH$_2$, and B is NH$_2$—C(S)—C(S)—NH$_2$.

27. The method according to claim 21, wherein the polyfunctional linker is a bis(thiuronium salt), Z is —S$^+$(—NH$_2$)(=NH)X$^-$, X is Br, Cl or I, R is an organic rest, and B is NH$_2$—C(S)—NH$_2$.

28. The method according to claim 21, wherein the polyfunctional linker is a tris(dithiooxamide) and the reaction is conducted at room temperature.

29. The method according to claim 21, wherein the polyfunctional linker is a tris(thiuronium salt) and the reaction is conducted at 60-100° C.

30. The method according to claim 20, wherein the interlinked nanoparticles are produced at room temperature.

31. The method according to claim 21, wherein the interlinked nanoparticles are produced at room temperature.

* * * * *